United States Patent
Maroo et al.

(10) Patent No.: US 11,763,945 B2
(45) Date of Patent: Sep. 19, 2023

(54) SYSTEM AND METHOD FOR LABELING MEDICAL DATA TO GENERATE LABELED TRAINING DATA

(71) Applicant: GE Precision Healthcare LLC, Wauwatosa, WI (US)

(72) Inventors: Sankit Maroo, Bangalore (IN); Jagan Selvaraj, Bangalore (IN); Kiran Muthigi, Bangalore, WI (US); Shaswat Lenka, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 921 days.

(21) Appl. No.: 16/715,896

(22) Filed: Dec. 16, 2019

(65) Prior Publication Data

US 2021/0182606 A1    Jun. 17, 2021

(51) Int. Cl.
*G16H 50/20* (2018.01)
*G16H 40/40* (2018.01)
*G06N 20/00* (2019.01)
*G06F 17/18* (2006.01)
*G06N 5/02* (2023.01)
*G06F 18/214* (2023.01)
(Continued)

(52) U.S. Cl.
CPC ............ *G16H 50/20* (2018.01); *G06F 17/18* (2013.01); *G06F 18/214* (2023.01); *G06F 18/23* (2023.01); *G06F 18/241* (2023.01); *G06N 5/02* (2013.01); *G06N 20/00* (2019.01); *G16H 40/40* (2018.01)

(58) Field of Classification Search
CPC .. G06K 9/6256; G06K 9/6218; G06K 9/6268; G06F 17/18; G06F 18/214; G06F 18/23; G06F 18/241; G06N 20/00; G06N 5/02; G16H 40/40; G16H 50/20
USPC .......................................................... 706/45
See application file for complete search history.

(56) References Cited

U.S. PATENT DOCUMENTS 9,535,902 B1      1/2017  Michalak et al.
10,430,690 B1 *  10/2019  Chen .................... G06V 10/774
(Continued)

OTHER PUBLICATIONS

Read, Jesse, et al., "Classifier Chains for Multi-label Classification", ECML PKDD 2009, Part II, LNAI 5782, Springer-Verlag Berlin Heidelberg, © 2009, pp. 254-269.*

(Continued)

*Primary Examiner* — Robert Stevens
(74) *Attorney, Agent, or Firm* — ANDRUS INTELLECTUAL PROPERTY LAW, LLP

(57) ABSTRACT

A method of automated labeling of medical data to generate labeled training data for training a learning algorithm is provided, wherein the medical data includes both machine-generated data elements and human-inputted data elements. The method includes using a knowledge graph to generate a first label for each machine-generated data element and each human-inputted data element. A set of trained classifier models are used to generate a second label for each machine-generated data element and each human-inputted data element. An unsupervised clustering model is used to generate a third label for each machine-generated data element and each human-inputted data element. A final label for each data element is then generated based on the first label, the second label, and the third label for the respective data element to output a labeled training dataset.

18 Claims, 5 Drawing Sheets

(51) Int. Cl.
  *G06F 18/23* (2023.01)
  *G06F 18/241* (2023.01)

(56) References Cited

U.S. PATENT DOCUMENTS

| | | | | |
|---|---|---|---|---|
| 10,521,734 | B2* | 12/2019 | Chen | G06V 10/82 |
| 10,593,431 | B1* | 3/2020 | Neumann | G16H 20/00 |
| 11,645,513 | B2* | 5/2023 | Glass | G06F 16/288 |
| | | | | 706/25 |
| 2008/0109388 | A1* | 5/2008 | Rosales | G06K 9/6226 |
| | | | | 706/12 |
| 2015/0370782 | A1* | 12/2015 | Fan | G06F 40/30 |
| | | | | 704/9 |
| 2016/0179835 | A1 | 6/2016 | Mika et al. | |
| 2018/0247209 | A1 | 8/2018 | Lecue et al. | |
| 2018/0300424 | A1 | 10/2018 | Alok et al. | |
| 2019/0147297 | A1* | 5/2019 | Rogers | G06N 20/00 |
| | | | | 706/12 |
| 2019/0347571 | A1* | 11/2019 | Qadir | G06N 20/00 |
| 2020/0294665 | A1* | 9/2020 | Neumann | G06N 5/02 |
| 2020/0312432 | A1* | 10/2020 | Wang | G06F 17/18 |
| 2020/0356851 | A1* | 11/2020 | Li | G06F 16/353 |
| 2022/0253699 | A1* | 8/2022 | Hoshen | G06N 3/08 |

OTHER PUBLICATIONS

Durand, Thibaut, et al., "Learning a Deep ConvNet for Multi-label Classification with Partial Labels", CVPR 2019, Long Beach, CA, Jun. 15-20, 2019, pp. 647-657.*

Weng, Heng, et al., "A Framework for Automated Knowledge Graph Construction Towards Traditional Chinese Medicine", HIS 2017, LNCS 10594, Springer International Publishing AG, © 2017, pp. 170-181.*

Dong-Hyun Lee, Pseudo-Label : The Simple and Ecient Semi-Supervised Learning Method for Deep Neural Networks, Workshop on Challenges in Representation Learning, ICML. vol. 3. 2013, 6 pages.

Bengio et al., Representation learning: A review and new perspectives, Cornell University, 2012, 30 pages.

Ratner et al., Snorkel: Rapid Training Data Creation with Weak Supervision, Cornell University, 2017, 17 pages.

* cited by examiner

SYSTEM AND METHOD FOR LABELING MEDICAL DATA TO GENERATE LABELED TRAINING DATA

BACKGROUND

The disclosed system and method generally relate to systems and methods for labeling medical data for use in training learning algorithms, such as machine learning algorithms and/or deep learning algorithms, and more particularly to scalable systems and methods for providing automatic labeling of medical data that includes both machine-generated data elements and human-inputted data elements.

Large and high-quality labeled training data is central to any efficient machine learning or deep learning pipeline. The performance of a supervised learning task depends immensely on the quality of the labeled dataset. Classification tasks, in particular, depend significantly on the quality of training data. However, in many business scenarios, the availability of quality training data is limited, mostly due to the constraints impinged upon by the data collection techniques and management. Classification tasks, in particular, depend significantly on the quality of training data. However, in many business scenarios, the availability of quality training data is limited, mostly due to the constraints impinged upon by the data collection techniques and management. As a result, human resource with deep domain expertise is required to annotate the dataset, which typically is a manual effort by a team of subject matter experts, and make it suitable for downstream analysis tasks such as predictive analytics, risk assessment etc. In many business scenarios, a dataset is often unlabeled and needs labeling by an external agent.

SUMMARY

This Summary is provided to introduce a selection of concepts that are further described below in the Detailed Description.

One embodiment of a method of automated labeling of medical data to generate labeled training data for training a learning algorithm is provided, wherein the medical data includes both machine-generated data elements and human-inputted data elements. The method includes using a knowledge graph to generate a first label for each machine-generated data element and each human-inputted data element. A set of trained classifier models are used to generate a second label for each machine-generated data element and each human-inputted data element. An unsupervised clustering model is used to generate a third label for each machine-generated data element and each human-inputted data element. A final label for each data element is then generated based on the first label, the second label, and the third label for the respective data element to output a labeled training dataset.

One embodiment of a system for processing medical equipment data relating to equipment failure to generate a labeled training dataset for training a machine learning algorithm or a deep learning algorithm is provided, wherein the medical equipment data includes machine-generated data elements and human-inputted data elements. A small labeled dataset is provided, wherein the label dataset includes at least machine-generated error codes and a set of key words. A knowledge graph that includes the small labeled dataset, a set of trained classifier models including at least three classifier models trained on the small labeled dataset, and an unsupervised clustering model trained on the small label dataset are provided and accessed by a processing system in order to generate a final label. The labeling occurs by generating a first label for each data element using the knowledge graph, and generating a second label for each data element using the set of trained classifier models. The final label for each data element is then generate based on at least the first label and the second label.

Various other features, objects and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
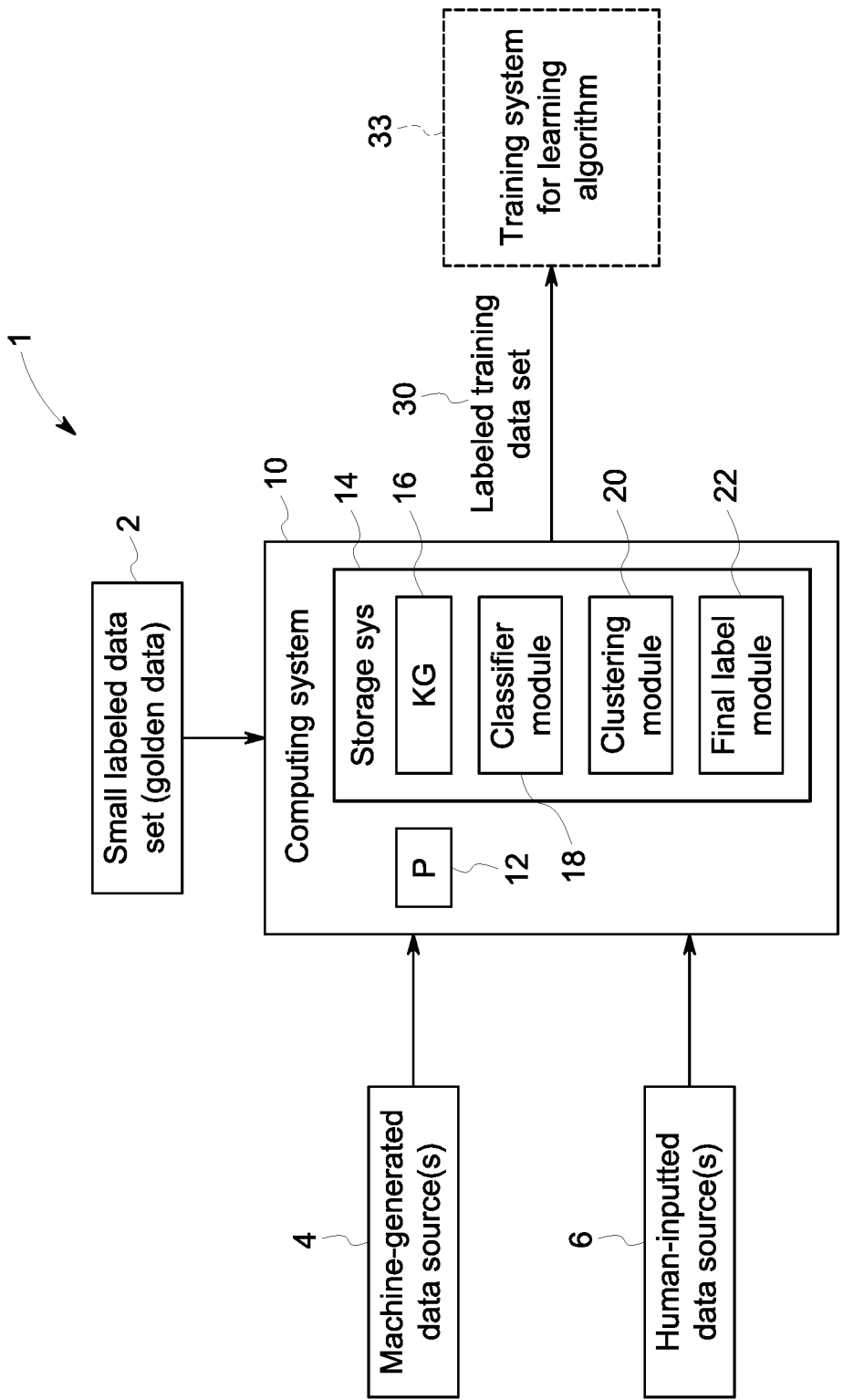
FIG. 1 schematically depicts an exemplary embodiment of a system for processing medical data to generate a labeled training dataset for training a learning algorithm.

Learning algorithms, including machine learning algorithms and deep learning algorithms, depend on quality training data in order to develop quality trained models and neural networks. However, generating quality training data is resource intensive and time consuming, especially when an empirical relationship does not exist between the features and their corresponding labels. Furthermore, the problem is exacerbated when the number of labels increases and/or when the input data is human-inputted unstructured text. The task of labeling training datasets often is performed manually by a team of experts tasked with reviewing and labeling, as well as cleaning, a dataset. In addition to requiring time and money, this process is not ideal because the differences between the results produced by different human experts such as due to differences in judgment and/or level of expertise, can yield inconsistencies within the training dataset.

Upon recognition of the foregoing problems and challenges in the relevant field, the inventors have developed a paradigm for producing high-quality labeled trading data—data points with reliably accurate labels—with minimal human involvement. The disclosed system and method use a small labeled dataset preferably providing knowledge of all labels (i.e., containing at least some data for each possible label to be generated by the system). This small labeled dataset is, for example, labeled by one or a small group of human experts so as to be highly accurate and consistent. For ease of reference herein, this small labeled dataset will be referred to as the "golden dataset." The golden dataset is then applied to label a much larger training dataset for training a learning algorithm. In certain examples, the size of the golden dataset may be at least 2% of the size of the training dataset to be labeled. In other embodiments, the golden dataset may be larger compared to the training dataset to be labeled, such as 10% of the total data elements in the dataset to be labeled. In still other embodiments, the size of the golden dataset may vary from the values listed herein, such as at least 15% or at least 20% of the size of the dataset to be labeled.

The information in the golden dataset is extrapolated and applied to the larger training dataset using a voting-based, multi-stage ensembling mechanism involving classifiers and a knowledge graph with domain-related data. A unique ensembling architecture labels data in real time with minimum human intervention, and thus tackles the two main issues with manual labeling of datasets—resource consumption and time consumption. A multi-staged ensembling technique involves both supervised and unsupervised models. This is combined with a knowledge graph implemented to capture the empirical knowledge in the datasets, such as key text phrases and/or meaningful data associations, and thereby organize the unstructured data into a high quality labeled dataset that can be utilized as a training dataset for a learning task.

The disclosed system and method can be used to identify targets (i.e. labels) from any dataset containing machine-generated data elements and/or human-inputted data elements. For example, the disclosed system and method can be used to process medical equipment data relating to equipment failure and to identify (i.e. label) a root cause of the failure to which each data element is related. For example, the machine-generated data may include error codes generated on or around the time of equipment failure. The human-inputted data may include, for example, service descriptions by service technicians describing symptoms and/or service actions taken to remedy the equipment failure. For example, the human inputted data utilized in the dataset may be a set of key words derived from such service descriptions. This same data will be represented in the golden dataset. For purposes of the knowledge graph, the golden dataset may be supplemented by other data elements that, for example, provide information that can be used to link the machine-generated data elements to the human-inputted data elements. For example, in relation to the equipment failure data, additional data sources may include standard operating procedures for the respective medical equipment, service manuals, or the like.

The disclosed system and method may likewise be used on medical data containing other sorts of medical or healthcare-related data including imaging-related data, patient monitoring-related data, waveform-related data, equipment service record data, etc. For example, the disclosed system and method may label patient monitoring data, such as human-inputted data elements relating to symptoms and/or patient care and machine-generated patient monitoring data. Alternatively or additionally, the disclosed system and method may be configured to label dosage data and/or patient medical record data.

FIG. 1 depicts an exemplary embodiment of a system 1 for automated labeling of medical data to generate a labeled training dataset 30 to be provided to a training system 33 that trains a learning algorithm, such as a machine learning algorithm or deep learning algorithm. Machine-generated data sources 4 and human-inputted data sources 6 provide data to be labeled. The small labeled dataset, or "golden data," 2 is also provided. A computing system 10 includes a processing system 12 and a storage system 14. The storage system 14 stores software, including computer-executable instructions to be executed by the processing system 12 to perform the methods described herein. For example, the storage system 14 stores the knowledge graph 16, a classifier module 18 containing a set of trained classifier models, and a clustering module 20 that includes an unsupervised clustering model. The knowledge graph 16, classifier module 18, and clustering module 20 are utilized together to generate the final label for each data element. In certain embodiments, the clustering module 20 may be eliminated and only the knowledge graph 16 and classifier module 18 may be utilized. Where the clustering module 20 is used it may provide additional certainty as to the accuracy of the final label.

The processing system 12 loads and executes software from the storage system 14, including the software modules 16, 18, 20, 22, which are software applications or other sets of computer executable instructions. The processing system 12 includes one or more processors, which may be a microprocessor, a general purpose central processing unit, an application-specific processor, a microcontroller, or any type of logic-based device. The processing system 14 may also include circuitry that retrieves and executes software from storage system 14. Processing system 12 can be implemented within a single processing device but can also be distributed across multiple processing devices or sub-systems that cooperate in executing program instructions. The storage system 14 can comprise any storage media, or group of storage media, readable by processing system 12 and capable of storing software. The storage system 14 can include volatile and non-volatile, removable and non-removable media implemented in any method or technology for storage of information, such as computer-readable instructions, data structures, program modules, or other data. Storage system 14 can be implemented as a single storage device but may also be implemented across multiple storage devices or sub-systems.

The knowledge graph 16 is used to generate a first label for each data element in the dataset to be labeled. The classifier module 18 outputs a second label for each data element in the dataset to be labeled. The clustering module 20 outputs a third label for each data element. A final label module 22 then generates a final label based on the first label, the second label, and the third label generated by the respective modules. For example, the final label may be determined by an unweighted voting process where each of the knowledge graph 16, classifier module 18, and clustering module 20 provide one vote on the label. The label with the most votes becomes the final label. The labeled data is then compiled into the labeled training dataset 30, which is provided for training the learning algorithm.

Figure 2:
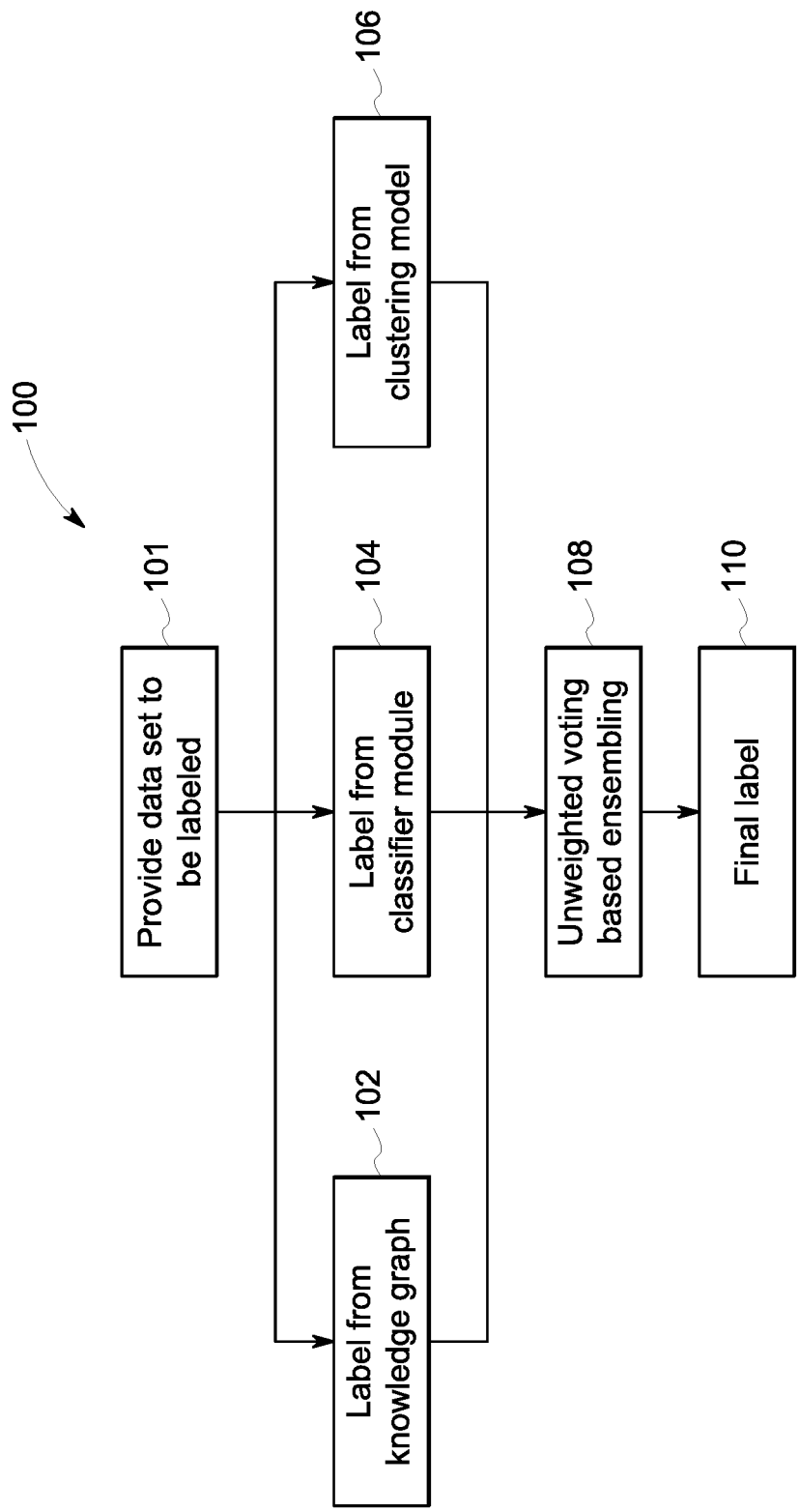
FIG. 2 is a flow chart depicting an exemplary method of automatically labeling medical data to generate a labeled training dataset.

The flow chart at FIG. 2 is a high level representation of one embodiment of a method 100 of automatically labeling medical data. The dataset to be labeled is provided at step 101. For each element in the dataset to be labeled, a first label is generated from the knowledge graph at step 102, a second label is generated from the classifier module at step 104, and a third label is generated from the clustering model at step 106. Each of the three labels is then provided to the final label module which generates the final label based on the outputs of the foregoing modules. In the example at FIG. 2, the final label is generated by unweighted voting based ensembling at step 108, where each of the first, second, and third labels are combined based on unweighted voting in order to generate the final label, which is outputted at step 110.

Figure 3:
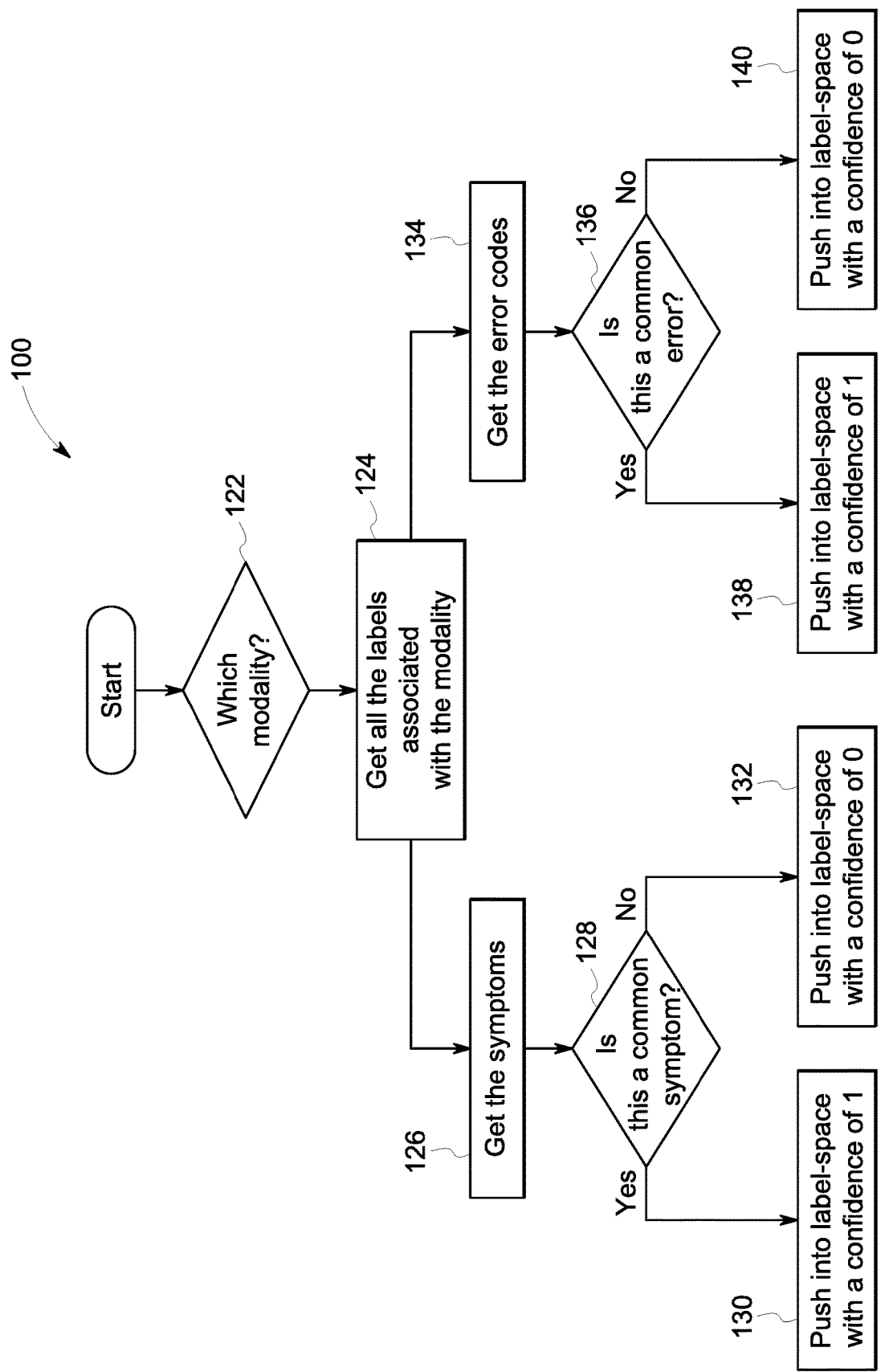
FIG. 3 is a flow chart depicting a first portion of an exemplary knowledge graph labeling process.

FIG. 3 depicts the first portion of the knowledge graph labeling process. The knowledge graph 16 is built based on the golden dataset and other information that might be relevant to the labeling process. To provide just one example, the knowledge graph 16 may be built using a database, such as a Cayley database, based on the golden data 2 and other domain-related data providing empirical knowledge. For example, where medical equipment data relating to equipment failure is to be labeled, the knowledge graph 16 may be built to capture empirical knowledge, such as text phrases of symptoms of equipment failure, error code associations, and the like, in order to organize the unstructured data into a graph structure. For instance, the knowledge graph 16 may be generated based on information from standard operating procedure documents, relevant key words extracted from service records inputted by field engineers and/or service technicians, and machine-generated error codes relating to the equipment failure.

In one embodiment, the knowledge graph 16 includes one or more sub knowledge graphs. For example, the knowledge graph 16 may be comprised of a standard operating procedures (SOP) and error code knowledge graph that contains common symptoms from the standard operating procedures. In one embodiment, there are two possible relationships represented in this knowledge graph space—"common symptoms" and "possible symptoms." A common symptom is a symptom that is most commonly found associated with the label, while a possible system is a symptom that may appear across multiple labels.

FIG. 3 exhibits use of this portion of the knowledge graph in order to identify machine-generated data such as error codes and human-inputted data, such as symptoms, with a prior knowledge that already exists in the knowledge graph. A confidence label of "1" is assigned if prior knowledge exists, and a confidence label of "0" is assigned if no prior knowledge exists. FIG. 3 illustrates this process with respect to medical equipment data relating to equipment failure. An initial step 122 is performed to identify the modality being assessed—i.e., what type and/or model of medical equipment the data relates to. All the labels associated with that modality are collected at step 124. The human-inputted data elements, such as the symptoms, are identified and/or isolated at step 126. Logic is then executed at step 128 to determine whether a confidence level of one or zero should be assigned based on whether the data element, which here is the symptom data, is a common symptom. For example, instructions may be executed to determine whether any other data exists labeled with that symptom. In other embodiments, that threshold data amount may be required in order to push the data element into the label space at step 130 with a confidence value of 1. If the symptom is not a common symptom, then the data element is pushed into label space at step 132 with a confidence value of zero.

Similar steps are performed for the machine-generated data, which in this example is error codes. The error codes are identified and/or isolated at step 134. Instructions are then executed at step 136 to determine whether the error code is a common error code. If so, then the data element is pushed into the label space at step 138 with a confidence value of one. If the error code does not meet the threshold for being a common error code at step 136, then the data element is pushed into the labeled space at step 140 with a confidence value of zero.

Figure 4:
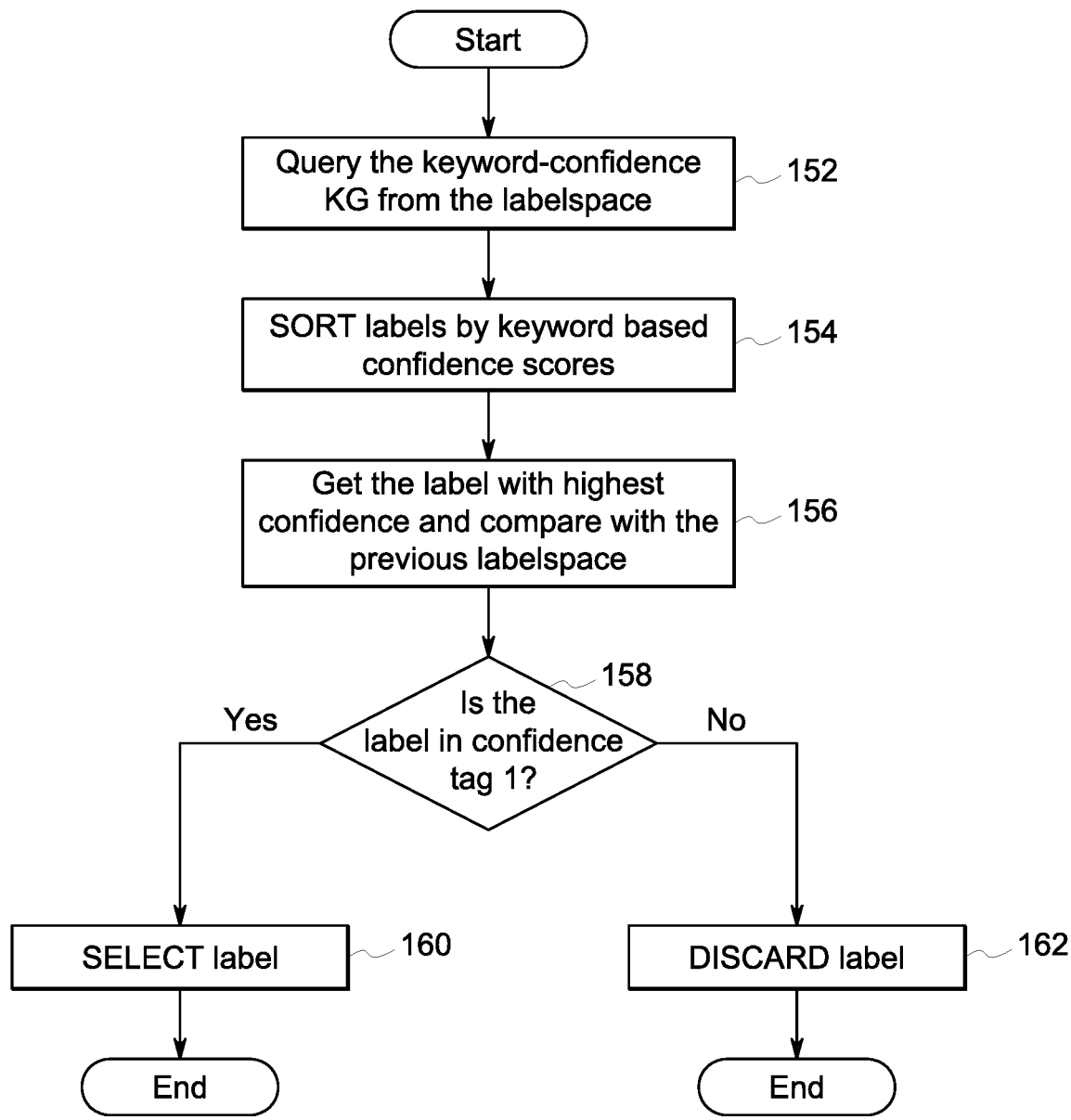
FIG. 4 is a flow chart depicting a second portion of the knowledge graph labeling process.

A knowledge graph 16 may further include a portion containing key words associated with each label from an "action taken" statement inputted by the service technician or field engineer. The relationship among the labels and key words in this portion of the knowledge graph 16 is associated with a frequency-based weight given to each key word-labeled pair. FIG. 4 exemplifies use this knowledge graph portion for completing labeling by the knowledge graph. This portion uses the confidence value produced by the first portion of the knowledge graph in stored in label space, as described above. The key word confidence is queried from the label space at step 152 from the first knowledge graph portion described above. The labels are sorted at step 154 based on the confidence scores. The label with the highest confidence score is identified at step 156 and compared with the label generated from the first knowledge graph portion built on the text/action taken. If the label has a confidence tag of "1" at step 158, then the label is selected at step 160 as the output of the knowledge graph 16 portion of the labeling algorithm. If instead the confidence value is "0" then the label is discarded at step 162. Thus, the relationship among the labels and key words here is associated with a frequency-based weight given to each key word label pair.

Figure 5:
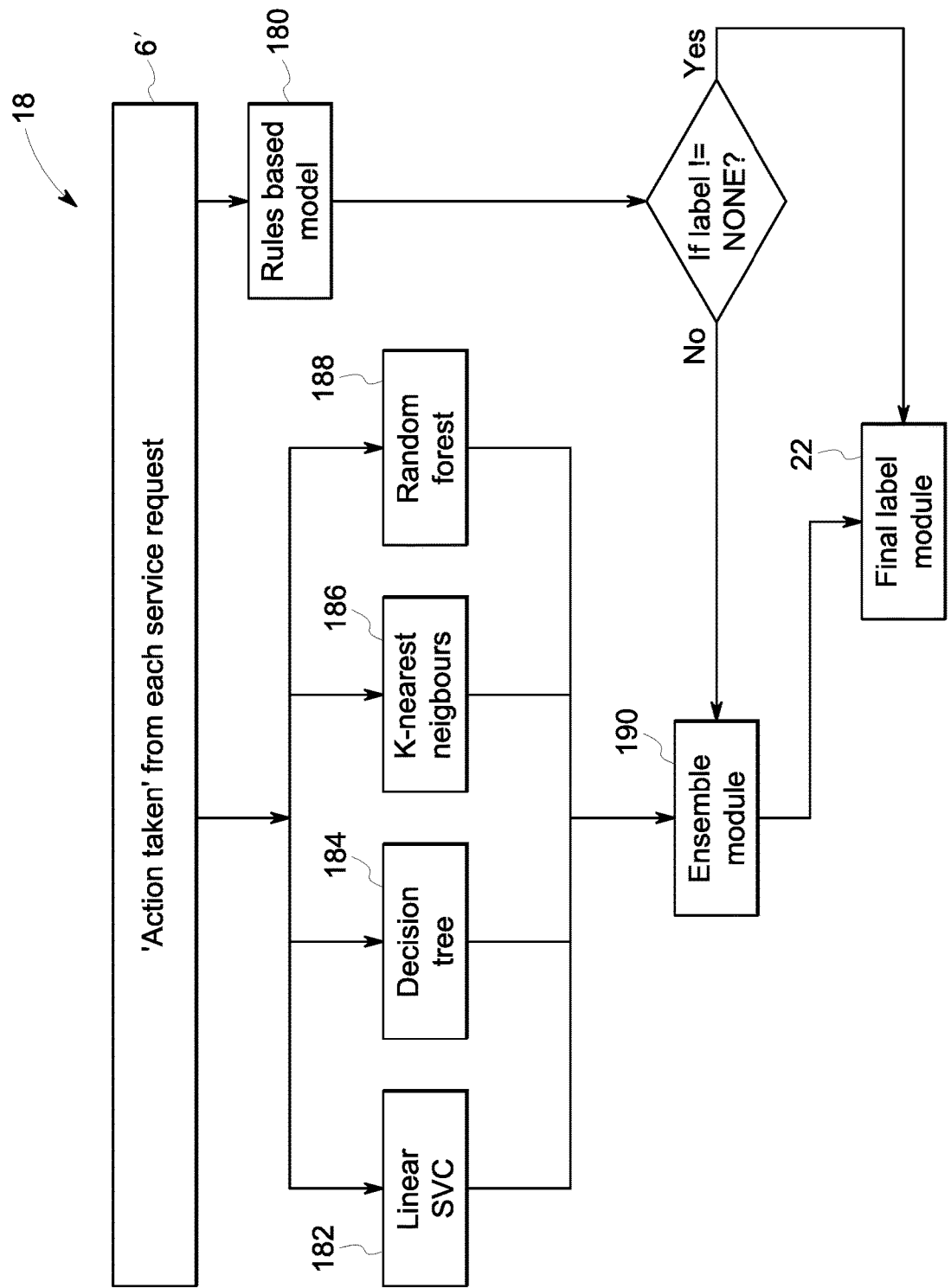
FIG. 5 schematically depicts an exemplary embodiment of a classifier module containing a set of trained classifier models for labeling training data.

FIG. 5 describes an exemplary structure for a classifier module 18, which comprises a set of classifier models 182, 184, 186, 188 and, in the depicted embodiment, also a rules based model 180. Each of the trained classifier models (e.g. 182-188) in one embodiment, each of the set of trained classifier models 182-188 is specialized for solving a different problem type, or detecting a different pattern type, than the others. Various classifier models may be utilized, depending on the data type being labeled. Additionally, various embodiments may include different numbers of classifiers models. The depicted embodiment includes four classifier models, including a linear SVC model 182, a decision tree model 184, a K-nearest neighbors model 186, and a random forest model 188 are utilized, where each model outputs a label prediction.

The output of the classifier models 182-188 are then combined in an ensembling step. In one embodiment, the set of trained classifiers models includes at least one model specialized for detecting linear patterns, which in the depicted embodiment is the linear SVC model 182, and also includes at least one model specialized for detecting non-linear patterns, which in the depicted embodiment is the random forest model 188. Additionally, the classifier module 18 may further include a model specialized for detecting non-linear and multivariate classifications, which in the depicted embodiment is the decision tree model 184. Alternatively or additionally, the classifier module 18 may further include a model specialized for detecting how closely different datasets are bunched together, which in the depicted embodiment is the K-nearest neighbors model 188. In various embodiments, different classification model types may be included and/or some of the listed model types may be excluded and replaced by different model types having similar performance functions and strengths.

The outputs of the various classifier models 182-188 are combined at the ensemble module 190. In various embodiments, different voting mechanisms may be utilized, such as an unweighted voting method, confidence voting methods, or ranked voting methods. In the depicted example, a weighted voting method is utilized that is based on the precision of each of the four models with respect to the predicted label. Each classifier model 182-188 outputs a label along with a probability score for the label. That probability score is then utilized by the ensemble module 190 to perform weighted voting. To provide one explanatory example, for a label generated based on linear pattern detection, the linear SVC model 182 will output a label with a high confidence score (because linear SVC is good at detecting linear patterns). The other models 184-188 will also output labels, but those labels are likely to have a lower confidence score. Thus, the output of the linear SVC model 182 will be weighted more heavily by the ensemble module 190 based on the confidence score outputted by the linear SVC model 182.

In order to catch and accurately label data elements that are underrepresented or noisy in the golden dataset, a rules based model 180 may be utilized. The rules based model 180 may be configured with rules to identify these underrepresented and/or noisy elements in the golden dataset and to assign a label accordingly. For example, the set of rules comprising the rules based model 180 may be manually-programed rules, such as to identify certain patterns or key words that are manually identified by the system administrator on system configuration as being insufficiently represented in the golden data to provide reliable detection and labeling. The set of rules is thus configured to identify these underrepresented scenarios and in the data to be labeled and then to assign an accurate label. For example, the model may identify a certain key word or error code that is underrepresented in the golden dataset and provide a rule to create a label for that data element.

In these situations where the data element being labeled matches one of the rules, the label assigned by the rules based model 180 overrides the label assigned by the ensemble module 190. This is generally the purpose of the rules based model 180 given that insufficient data is available to reliably assign a label. For all other data elements that are adequately represented, the rules based model 180 will not output a label and the set of classifier models 182-188 generate the label that gets outputted by the classifier module 18 to the final label module 22.

In the depicted example, which is relevant to labeling medical equipment data relating to equipment failure, and the classifier module 18 utilizes the "action taken" key word from each service request, which is a human-inputted data element 6'. Each of the models 182-188 is trained on the golden dataset to assign an "action to taken" label to the "action taken" data element. Thus, each of the models 182-188 is configured to receive the "action taken" as the input and to predict a label designating "action to take" along with a probability score, as described above. Each of the "action to take" label and probability score from each of the classifier models 182-188 is provided to the ensemble module 190, which generates a label on behalf of the classifier module 18. For example, a weighted voting mechanism may be utilized such that the label with the highest score, such as the highest total probability score, is chosen. As described above, the rules based model may be configured to override the ensembled classifier model outputs for certain underrepresented patterns. In this example, the rules based model 180 receives "action taken" as the input and predicts a label if it finds a rule that matches that data element. If not, then the rules based model 180 outputs a null value or some other predetermined value indicating that no pattern matching and underrepresented or noisy data element was located.

Finally, a clustering module 20 that includes an unsupervised clustering model configured to utilize the golden dataset to generate a third label. This third label can be utilized to increase the confidence level in the final label outputted by the system 1. While unsupervised clustering models utilizing small datasets may, by themselves, be insufficient to provide a reliable label, when used in combination with the knowledge graph 16 and the classifiers module 18, as described herein, a very reliable final label can be generated. Namely, any inaccuracy in the automatic and unsupervised learning for the unsupervised clustering module may be overridden and compensated for by the outputs of the knowledge graph 16 and/or the classifier module 18.

Accordingly, the system and method described herein provide a specialized and reliable automated labeling mechanism that can scale a small, reliably-labeled database to provide accurate labeling of a very large dataset for use in training learning algorithms. The disclosed system and method provide high quality and consistent labeling that eliminates the variability that occurs when a group of human experts are utilized to label the data. Moreover, the system and method provide labeling at a reduced cost and in a much shorter time period than the current manual labeling process. Accordingly, the labeled dataset provided by the current method and system is more accurate, less noisy, and is more analyzable from a data science perspective because the results are transparent.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of automated labeling of medical data to generate labeled training data for training a learning algorithm, wherein the medical data includes medical equipment data relating to equipment failure and includes both machine-generated data elements and human-inputted data elements, the method comprising:
   using a knowledge graph to generate a first label for each machine-generated data element and each human-inputted data element;
   using a set of trained classifier models to generate a second label for each machine-generated data element and each human-inputted data element;
   using an unsupervised clustering model to generate a third label for each machine-generated data element and each human-inputted data element; and
   generating a final label for each machine-generated data element and each human-inputted data element based on the first label, the second label, and the third label for the respective data element to output a labeled training dataset, and wherein the final label identifies a root-cause of the failure to which the machine-generated or human-inputted data element is related.

2. The method of claim 1, further comprising using the labeled training data to train a machine learning algorithm or a deep learning algorithm.

3. The method of claim 1, wherein the final label is generated by unweighted voting based on the first label, the second label, and the third label.

4. The method of claim 1, wherein the knowledge graph, each of the set of trained classifier models, and the unsupervised clustering model are trained based on a small labeled dataset.

5. The method of claim 1, wherein the medical equipment data relating to equipment failure includes machine-generated error codes and keywords from human-inputted service descriptions.

6. The method of claim 5, wherein the small labeled dataset includes machine-generated error codes and a set of keywords from human-inputted service descriptions that represent a full range of failures for a given medical equipment modality.

7. The method of claim 1, wherein generating the third label using the set of trained classifier models includes, with each of at least three trained classifier models, generating a classifier label and a probability score and then using weighted voting to generate the third label based on the at least three classifier labels and corresponding probability scores.

8. The method of claim 7, further comprising providing a rule-based override of the third label generated by the set of trained classifier models to capture underrepresented events.

9. The method of claim 7, wherein the medical equipment data relating to equipment failure includes machine-generated error codes and keywords from human-inputted service descriptions.

10. A system for processing medical equipment data relating to equipment failure to generate a labeled training dataset for training a machine learning algorithm or a deep learning algorithm for assessing medical equipment failure, wherein the medical equipment data includes machine-generated data elements and human-inputted data elements, the system comprising:
- a small labeled dataset, wherein the small labeled dataset includes machine-generated error codes and a set of keywords;
- a knowledge graph that includes the small labeled dataset;
- a set of trained classifier models including at least three classifier models trained on the small labeled dataset;
- a processing system configured to:
  - generate a first label for each machine-generated data element and each human-inputted data element using the knowledge graph;
  - generate a second label for each machine-generated data element and each human-inputted data element using the set of trained classifier models; and
  - generate a final label for each machine-generated data element and each human-inputted data element based on at least the first label and the second label for the respective data element to output a labeled training dataset, wherein the final label identifies a root-cause of the failure to which the machine-generated or human-inputted data element is related.

11. The system of claim 10, wherein the small labeled dataset includes the machine-generated error codes and the set of keywords that represent a full range of failures for a given medical equipment modality, and includes between 2% and 20% as many data elements as the medical equipment data to be automatically labeled.

12. The system of claim 10, wherein the medical equipment data relating to equipment failure includes machine-generated error codes and keywords from human-inputted service descriptions.

13. The system of claim 10, further comprising an unsupervised clustering model trained on the small labeled dataset, and wherein the processing system is further configured to generate a third label for each machine-generated data element and each human-inputted data element using the unsupervised clustering model.

14. The system of claim 13, wherein using the set of trained classifier models to generate the third label includes, with each of the at least three trained classifier models, generating a classifier label and a probability score and then using weighted voting to generate the third label based on the at least three classifier labels and corresponding probability scores.

15. The system of claim 14, wherein the set of trained classifier models includes a model for detecting linear patterns, a model for detecting non-linear patterns, and a model for detecting multi-variate classifications.

16. The system of claim 15, wherein the set of trained classifier models includes a decision SVC model, a decision tree model, a K-nearest neighbors model, and a random forest model.

17. The system of claim 14, further comprising a rule-based model configured to override the third label generated by the set of trained classifier models to capture underrepresented equipment failures.

18. The system of claim 10, wherein the final label is generated by unweighted voting based on the first label, the second label, and the third label.

\* \* \* \* \*